(12) United States Patent
Macina et al.

(10) Patent No.: US 6,858,386 B1
(45) Date of Patent: Feb. 22, 2005

(54) METHOD OF DIAGNOSING, MONITORING, STAGING, IMAGING AND TREATING COLON CANCER

(75) Inventors: Roberto A. Macina, San Jose, CA (US); Yongming Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/618,596

(22) Filed: Jul. 17, 2000

Related U.S. Application Data

(63) Continuation-in-part of application No. PCT/US99/10498, filed on May 12, 1999.
(60) Provisional application No. 60/086,266, filed on May 21, 1998.

(51) Int. Cl.[7] .............................. C12Q 1/68; C12Q 1/00; G01N 33/567; G01N 33/574; G01N 33/53

(52) U.S. Cl. ................................ 435/6; 435/4; 435/7.1; 435/7.21; 435/7.23; 435/7.92; 435/7.93; 435/40.5; 435/40.51; 435/70.1; 436/63; 436/64; 436/86; 436/174; 530/300; 530/350; 536/1; 536/18.7; 536/22.1; 536/23.1; 536/23.5

(58) Field of Search ...................... 435/4, 6, 7.1, 7.21, 435/7.23, 7.92, 7.93, 40.5, 40.51, 70.1, 325; 436/63, 64, 174, 86; 536/1, 18.7, 22.1, 23.1, 23.5; 530/300, 350

(56) References Cited

U.S. PATENT DOCUMENTS

| | | | | |
|---|---|---|---|---|
| 4,690,914 | A | 9/1987 | Callut et al. ............... | 502/400 |
| 5,585,103 | A | 12/1996 | Raychaudhuri .......... | 424/278.1 |
| 5,733,748 | A | * 3/1998 | Yu et al. | |
| 5,985,270 | A | 11/1999 | Srivastava ............... | 424/93.71 |
| 2003/0044783 | A1 | 3/2003 | Williams | |
| 2003/0109690 | A1 | 6/2003 | Rubin | |

FOREIGN PATENT DOCUMENTS

| | | |
|---|---|---|
| WO | WO 96/39419 A1 | 12/1996 |
| WO | WO 96/39419 | * 12/1996 |
| WO | WO 99/60161 | 11/1999 |
| WO | WO 00/07632 | 2/2000 |
| WO | WO 00/28031 A2 | 5/2000 |
| WO | WO 01/96388 A2 | 12/2001 |
| WO | WO 01/096388 A3 | 12/2001 |

OTHER PUBLICATIONS

Oka et al. Expression of E–Cadherin cell adhesion molecules in human breast cacner tissues and its relationship to metastasis, Cancer Research 53: 1696–1701, Apr. 1, 1993.*
Tockman et al. Consideration in Bringing a Cancer Biomarker to Clinical Application, Cancer Research, Suppl. 52: 2711s–2718s, May 1, 1992.*
Weeraratna et al. Loss of Uteroglobin Expression inprostate cancer: relationship to advancing grade. Clinical Cancer Research 3: 2295–2300, Dec. 1997.*
Bayraktutan et al., "Molecular Characterization and Localization of the NAD (P) H Oxidase Components gp91–phox and p22–phox in Endothelial Cells", Arteriosclerosis, Thrombosis, and Vascular Biology 2000 20(8)1903 1–11 (reprint provided herewith as pp. 1–18).
Kikuchi et al., "NADPH oxidase subunit, gp91 (phox) homologue, preferentially expressed in human colon epithelial cells", Gene 2000 254(1–2) :237–243.
Royer–Pokora et al., "Cloning the gene for an inherited human disorder–chronic granulomatous disease–on the basis of its chromosomal location", Nature 1986 322:32–38.
NCBI Accession NO. NM_007052 [gi:5902005] Dec. 22, 1999—Apr. 28, 2000 with Revision History.
NCBI Accession NO. NM_013955 [gi:7669509] Apr. 28, 2000 with Revision History.
NCBI Accession No. NM_013954 [GI:7669507] Apr. 28, 2000 with Revision History.
NCBI Accession No. AF127763 [gi:5031251] Jun. 10, 1999–Oct. 29, 1999 with Revision History.
NCBI Accession No. AF166327 [gi:6672077] Jan. 6, 2000 with Revision History.
NCBI Accession No. AF166328 [gi:6672079] Jan. 6, 2000 with Revision History.
NCBI Accession No. AJ438989 [gi:19572339] Mar. 15, 2002 with Revision History.
NCBI Accession No. AF166326 [gi:6672075] Jan. 6, 2000 with Revision History.
NCBI Accession No. Q9Y5S8 [gi:8134597] Feb. 15, 2000–May 30, 2000 with Revision History.
NCBI Accession No. NP_000388 [gi:4557507] Mar. 8, 1999–Feb. 16, 2000 with Revision History.
Bánfi et al., "A Mammalian H+Channel Generated Through Alternative Splicing of the NADPH Oxidase Homolog NOH–1", Science 2000 287:138–142.
Suh et al., "Cell Transformation by the superoxide–generating oxidase Mox1", Nature 1999 401:79–81.
Griffin et al., "Initial Clinical Study of Indium–111–Labeled Clone 110 Anticarcinoembryonic Antigen Antibody in Patients with Colorectal Cancer", *J. Clin. Onc.* 1991 9:631–640.
Lauffer, R.B., "Targeted Relaxation Enhancement Agents for MRI*", *Magnetic Resonance in Medicine* 1991 22:339–342.
Rosenberg, S. A., et al., "Use of Tumor–Infiltrating Lymphocytes and Interleukin–2 in the Immunotherapy of Patients with Metastatic Melanoma", *N. England J. Med* 1988, 319:1676–1680.

(List continued on next page.)

*Primary Examiner*—Alana M. Harris
(74) *Attorney, Agent, or Firm*—Licata & Tyrrell P.C.

(57) ABSTRACT

The present invention provides new methods for detecting, diagnosing, monitoring, staging, prognosticating, imaging and treating colon cancer.

1 Claim, No Drawings

OTHER PUBLICATIONS

Sumerdon et al., "An Optimized Antibody–Chelator Conjugate for Imaging of Carcinoembryonic Antigen with Indium–111", *Nucl. Med. Biol.* 1990, 17:247–254.

Arbiser et al., Reactive oxygen generated by Nox1 triggers the angiogenic switch, PNAS, Jan. 22, 2002, vol. 99 No. 2, pp. 715–720.

Lambeth et al., Novel homologs of gp91phox, TiBS, 2000, 25, pp. 459–461.

Suh et al., Cell transformation by the superoxide–generating oxidase Mox1, Nature, Sep. 2, 1999, vol. 401, pp. 79–82.

Database Genebank, Accession No. XP_010073,NCBI, NADPH oxidase 1 isoform, long [*Homo sapiens*], Aug. 27, 2001, see sequence.

Database Genebank, Accession No. NP_008983,Shu et al., NADPH oxidase 1 isoform long; mitogenic oxidase (pyridine nucleotide–dependent superoxide–generating); NADPH oxidase homolog–1 [Homo sapiens], Feb. 3, 2001, see sequence.

Database Genebank, Accession No. CAB06073,Lloyd, D, dJ146H21.2 (similar to Cytochrome B–245 heavy chain) [*Homo sapiens*], Nov. 23, 1999, see sequence.

Database Genebank, Accession No. NP_098249,Suh et al., NADPH oxidase 1 isoform long; mitogenic oxidase (pyridine nucleotide–dependent superoxide–generating); NADPH oxidase homolog–1 [*Homo sapiens*], Feb. 03, 2001, see sequence.

Database Genebank, Accession No. Q9WV87,Suh et al., NADPH oxidase homolog 1 (NOX–1) (NOH–1) (NADH/NADPH mitogenic oxidase subunit P65–MOX) (Mitogenic oxidase 1) (MOX1), May 30, 2000, see sequence.

Database Genbank, Accession No. O46522,Davis, Cytochrome B–245 heavy chain (P22 phagocyte B–cytochrome) (neutrophil cytochrome B, 91 kDa polypeptide)..., May 30, 2000, see sequence.

* cited by examiner

METHOD OF DIAGNOSING, MONITORING, STAGING, IMAGING AND TREATING COLON CANCER

This application is a continuation-in-part of PCT Application PCT/US99/10498, filed May 12, 1999, which claims the benefit of priority from U.S. Provisional Application Ser. No. 60/086,266 filed May 21, 1998.

FIELD OF THE INVENTION

This invention relates, in part, to newly developed assays for detecting, diagnosing, monitoring, staging, prognosticating, imaging and treating cancers, particularly colon cancer.

BACKGROUND OF THE INVENTION

Cancer of the colon is a highly treatable and often curable disease when localized to the bowel. It is one of the most frequently diagnosed malignancies in the United States as well as the second most common cause of cancer death. Surgery is the primary treatment and results in cure in approximately 50% of patients. However, recurrence following surgery is a major problem and often is the ultimate cause of death.

The prognosis of colon cancer is clearly related to the degree of penetration of the tumor through the bowel wall and the presence or absence of nodal involvement. These two characteristics form the basis for all staging systems developed for this disease. Treatment decisions are usually made in reference to the older Duke's or the Modified Astler-Coller (MAC) classification scheme for staging.

Bowel obstruction and bowel perforation are indicators of poor prognosis in patients with colon cancer. Elevated pretreatment serum levels of carcinoembryonic antigen (CEA) and of carbohydrate antigen 19-9 (CA 19-9) also have a negative prognostic significance.

Age greater than 70 years at presentation is not a contraindication to standard therapies. Acceptable morbidity and mortality, as well as long-term survival, are achieved in this patient population.

Because of the frequency of the disease (approximately 160,000 new cases of colon and rectal cancer per year), the identification of high-risk groups, the demonstrated slow growth of primary lesions, the better survival of early-stage lesions, and the relative simplicity and accuracy of screening tests, screening for colon cancer should be a part of routine care for all adults starting at age 50, especially those with first-degree relatives with colorectal cancer.

Procedures used for detecting, diagnosing, monitoring, staging, and prognosticating colon cancer are of critical importance to the outcome of the patient. For example, patients diagnosed with early colon cancer generally have a much greater five-year survival rate as compared to the survival rate for patients diagnosed with distant metastasized colon cancer. New diagnostic methods which are more sensitive and specific for detecting early colon cancer are clearly needed.

Colon cancer patients are closely monitored following initial therapy and during adjuvant therapy to determine response to therapy and to detect persistent or recurrent disease of metastasis. There is clearly a need for a colon cancer marker which is more sensitive and specific in detecting colon cancer, its recurrence, and progression.

Another important step in managing colon cancer is to determine the stage of the patient's disease. Stage determination has potential prognostic value and provides criteria for designing optimal therapy. Generally, pathological staging of colon cancer is preferable over clinical staging because the former gives a more accurate prognosis. However, clinical staging would be preferred were it at least as accurate as pathological staging because it does not depend on an invasive procedure to obtain tissue for pathological evaluation. Staging of colon cancer would be improved by detecting new markers in cells, tissues, or bodily fluids which could differentiate between different stages of invasion.

Accordingly, there is a great need for more sensitive and accurate methods for the staging of colon cancer in a human to determine whether or not such cancer has metastasized and for monitoring the progress of colon cancer in a human which has not metastasized for the onset of metastasis.

In the present invention, methods are provided for detecting, diagnosing, monitoring, staging, prognosticating, imaging and treating colon cancer via a colon specific gene referred to herein as CSG. For purposes of the present invention, CSG refers, among other things, to native protein expressed by the gene comprising a polynucleotide sequence of SEQ ID NO: 1. By "CSG" it is also meant herein polynucleotides which, due to degeneracy in genetic coding, comprise variations in nucleotide sequence as compared to SEQ ID NO: 1 but which still encode the same protein. In the alternative, what is meant by CSG as used herein, means the native mRNA encoded by the gene comprising the polynucleotide sequence of SEQ ID NO: 1, levels of the gene comprising the polynucleotide sequence of SEQ ID NO: 1, or levels of a polynucleotide which is capable of hybridizing under stringent conditions to the antisense sequence of SEQ ID NO: 1. SEQ ID NO: 1 is also referred to as Cln106.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of colon cancer by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with colon cancer.

Further provided is a method of diagnosing metastatic colon cancer in a patient having colon cancer which is not known to have metastasized by identifying a human patient suspected of having colon cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with colon cancer which has metastasized.

Also provided by the invention is a method of staging colon cancer in a human which has such cancer by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing or at a more advanced stage and a decrease in the levels of CSG is associated with a cancer which is regressing or at a lower stage or in remission.

Further provided is a method of monitoring colon cancer in a human having such cancer for the onset of metastasis. The method comprises identifying a human patient having such cancer that is not known to have metastasized; periodically analyzing a sample of cells, tissues, or bodily fluids from such patient for CSG; comparing the CSG levels in such cells, tissues, or bodily fluids with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of colon cancer in a human having such cancer by looking at levels of CSG in a human having such cancer. The method comprises identifying a human patient having such cancer; periodically analyzing a sample of cells, tissues, or bodily fluids from such patient for CSG; comparing the CSG levels in such cells, tissues, or bodily fluids with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are methods of designing new therapeutic agents targeted to a CSG for use in imaging and treating colon cancer. For example, in one embodiment, therapeutic agents such as antibodies targeted against CSG or fragments of such antibodies can be used to treat, detect or image localization of CSG in a patient for the purpose of detecting or diagnosing a disease or condition. In this image embodiment, an increase in the amount of labeled antibody detected as compared to normal tissue would be indicative of tumor metastases or growth. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels and therapeutic agents including, but not limited to, radioisotopes and paramagnetic metals. Therapeutic agents such as small molecules and antibodies which decrease the concentration and/or activity of CSG can also be used in the treatment of diseases characterized by overexpression of CSG. Such agents can be readily identified in accordance with teachings herein.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to, inter alia, diagnostic assays and methods, both quantitative and qualitative for detecting, diagnosing, monitoring, staging and prognosticating cancer, and in particular colon cancer, by comparing levels of CSG in a human patient with those of CSG in a normal human control. It has now been found the CSG levels are elevated in colon cancer tissue as compared to normal tissue. For purposes of the present invention, what is meant by CSG levels is, among other things, native protein expressed by the gene comprising a polynucleotide sequence of SEQ ID NO: 1. By "CSG" it is also meant herein polynucleotides which, due to degeneracy in genetic coding, comprise variations in nucleotide sequence as compared to SEQ ID NO: 1, but which still encode the same protein. The native protein being detected may be whole, a breakdown product, a complex of molecules or chemically modified. In the alternative, what is meant by CSG as used herein, means the native mRNA encoded by the gene comprising the polynucleotide sequence of SEQ ID NO: 1 levels of the gene comprising the polynucleotide sequence of SEQ ID NO: 1 or levels of a polynucleotide which is capable of hybridizing under stringent conditions to the antisense sequence of SEQ ID NO: 1. SEQ ID NO:1 is also referred to as Cln106. Levels of CSG are preferably determined in at least one of cells, tissues and/or bodily fluids, including determination of normal and abnormal levels. Thus, for instance, a diagnostic assay in accordance with the invention for diagnosing overexpression of CSG protein compared to normal control bodily fluids, cells, or tissue samples may be used to diagnose the presence of colon cancer.

All the methods of the present invention may optionally include determining the levels of other cancer markers as well as CSG. Other cancer markers, in addition to CSG, useful in the present invention are known to those of skill in the art.

Diagnostic Assays

The present invention provides methods for diagnosing the presence of cancer, and in particular colon cancer, by analyzing for changes in levels of CSG in cells, tissues or bodily, fluids compared with levels of CSG in cells, tissues or bodily fluids of preferably the same type from a normal human control, wherein an increase in levels of CSG in the patient versus the normal human control is associated with the presence of colon cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastatic colon cancer in a patient having colon cancer which has not yet metastasized for the onset of metastasis. In the method of the present invention, a human cancer patient suspected of having colon cancer which may have metastasized (but which was not previously known to have metastasized) is identified. This is accomplished by a variety of means known to those of skill in the art.

In the present invention, determining the presence of CSG levels in cells, tissues or bodily fluid, is particularly useful for discriminating between colon cancer which has not metastasized and colon cancer which has metastasized. Existing techniques have difficulty discriminating between colon cancer which has metastasized and colon cancer which has not metastasized and proper treatment selection is often dependent upon such knowledge.

In the present invention, the cancer marker levels measured in such cells, tissues or bodily fluid is CSG, and are compared with levels of CSG in preferably the same cells, tissues or bodily fluid type of a normal human control. That is, if the cancer marker being observed is CSG in serum, this level is preferably compared with the level of CSG in serum of a normal human control. An increase in the CSG in the patient versus the normal human control is associated with colon cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have colon cancer which has not metastasized.

Staging

The invention also provides a method of staging colon cancer in a human patient. The method comprises identifying a human patient having such cancer and analyzing cells, tissues or bodily fluid from such human patient for CSG. The CSG levels determined in the patient are then compared with levels of CSG in preferably the same cells, tissues or bodily fluid type of a normal human control, wherein an increase in CSG levels in the human patient versus the normal human control is associated with a cancer which is progressing or at a higher stage and a decrease in the levels of CSG (but generally still increased over true normal levels) is associated with a cancer which is regressing or at a lower stage or in remission.

Monitoring

Further provided is a method of monitoring colon cancer in a human patient having such cancer for the onset of metastasis. The method comprises identifying a human patient having such cancer that is not known to have metastasized; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which has metastasized. In this method, normal human control samples may also include prior samples from the same patient.

Further provided by this invention is a method of monitoring the change in stage of colon cancer in a human patient having such cancer. The method comprises identifying a human patient having such cancer; periodically analyzing cells, tissues or bodily fluid from such human patient for CSG; and comparing the CSG levels determined in the human patient with levels of CSG in preferably the same cells, co tissues or bodily fluid type of a normal human control, wherein an increase in CSG levels in the human patient versus the normal human control is associated with a cancer which is progressing in stage and a decrease in the levels of CSG is associated with a cancer which is regressing in stage or in remission. In this method, normal human control samples may also include prior patient samples.

Monitoring a patient for onset of metastasis is periodic and preferably done on a quarterly basis. However, this may be done more or less frequently depending on the cancer, the particular patient, and the stage of the cancer.

Prognostic Testing and Clinical Trial Monitoring

The methods described herein can further be utilized as prognostic assays to identify subjects having or at risk of developing a disease or disorder associated with increased levels of CSG. The present invention provides a method in which a test sample is obtained from a human patient and a CSG is detected. The presence of higher CSG levels as compared to normal human controls is diagnostic for the human patient being at risk for developing cancer, specifically colon cancer.

The effectiveness of therapeutic agents to decrease expression or activity of the CSG of the invention can also be monitored by analyzing levels of expression of the CSG in a human patient, e.g. during treatment, in clinical trials or in in vitro screening assays such/as in human cells. In this way, the CSG expression pattern can serve as a marker, indicative of the physiological response of the human patient, or cells as the case may be, to the agent being tested or being used to treat the patient.

Detection of genetic lesions or mutations

The methods of the present invention can also be used to detect genetic lesions or mutations in a CSG, thereby determining if a human with the genetic lesion is at risk for colon cancer or has colon cancer. Genetic lesions can be detected, for example, by ascertaining the existence of a deletion and/or addition and/or substitution of one or more nucleotides from the CSG of this invention, a chromosomal rearrangement of a CSG, aberrant modification of CSG (such as of the methylation pattern of the genomic DNA), the presence of a non-wild type splicing pattern of a mRNA transcript of a CSG, allelic loss of a CSG, and/or inappropriate post-translational modification of a CSG protein. Methods to detect such lesions in the CSG of this invention are known to those of skill in the art.

Assay Techniques

Assay techniques that can be used to determine levels of gene expression (including protein levels), such as CSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches, two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent, for example horseradish peroxidase enzyme or alkaline phosphatase.

To carry out the ELISA, antibody specific to CSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to a detectable reagent such as horseradish peroxidase is placed in the dish resulting in binding of the reporter antibody to any monoclonal antibody bound to CSG. Unattached reporter antibody is then washed out. Reagents for peroxidase activity, including a calorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay can also be employed wherein antibodies specific to CSG are attached to a solid support and labeled CSG and a sample derived from the host are passed over the solid support. The amount of label detected which is attached to the solid support can be correlated to a quantity of CSG in the sample.

Using all or a portion of a nucleic acid sequence of a CSG of the present invention as a hybridization probe, nucleic acid methods can also be used to detect levels of CSG mRNA as a marker for colon cancer. Polymerase chain reaction (PCR) and other nucleic acid methods, such as ligase chain reaction (LCR) and nucleic acid sequence based amplification (NASBA), can be used to detect cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence and/or absence of a specific type of cell.

Hybridization to clones or oligonucleotides arrayed on a solid support (i.e. gridding) can be used to both detect the expression of and quantitate the level of expression of the gene. In this approach, all or a portion of a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those skilled in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of CSG/Colon Cancer Therapy

Identification of this CSG is also useful in the rational design of new therapeutics for imaging and treating cancers, and in particular colon cancer. For example, in one embodiment, antibodies which specifically bind to the CSG can be raised and used in vivo in patients suspected of suffering from colon cancer associated with increased levels of CSG. Antibodies which specifically bind the CSG can be injected into a patient suspected of having colon cancer for diagnostic and/or therapeutic purposes. Thus, another aspect of the present invention provides for a method for preventing the onset and treatment of colon cancer in a human patient in need of such treatment by administering to the patient an effective amount of an antibody to CSG. By "effective amount" it is meant the amount or concentration of antibody needed to bind to the target antigens expressed on the tumor to cause tumor shrinkage for surgical removal, or disappearance of the tumor. The binding of the antibody to the overexpressed CSG is believed to cause the death of the cancer cell expressing such CSG. The antibodies can be administered alone or with other therapeutic agents known to those in the art.

The preparation and use of antibodies for in vivo diagnosis and treatment is well known in the art. For example, antibody-chelators labeled with Indium-111 have been described for use in the radioimmunoscintographic imaging of carcinoembryonic antigen expressing tumors (Sumerdon et al.

Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against CSG can be used in a similar manner. Labeled antibodies which specifically bind CSG can be injected into patients suspected of having colon cancer for the purpose of diagnosing, monitoring or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Presence of the label, as compared to imaging of normal tissue, permits determination of the spread of the cancer. The amount of label within an organ or tissue also allows determination of the presence or absence of cancer in that organ or tissue.

Antibodies which can be used in in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Screening Assays

The present invention also provides methods for identifying modulators which bind to CSG protein of the invention or have a modulatory effect on the expression or activity of CSG protein of this invention. Modulators which decrease the expression or activity of CSG protein of the invention are believed to be useful in treating colon cancer. Such screening assays are known to those of skill in the art and include, without limitation, cell-based assays and cell free assays.

Small molecules predicted via computer imaging to specifically bind to regions of CSG can also be designed, synthesized and tested for use in the imaging and treatment of colon cancer. Further, libraries of molecules can be screened for potential anticancer agents by assessing the ability of the molecule to bind to the CSG identified herein. Molecules identified in the library as being capable of binding to CSG are key candidates for further evaluation for use in the treatment of colon cancer. In a preferred embodiment, these molecules will downregulate expression and/or activity of CSG in cells.

Adoptive Immunotherapy and Vaccines

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, N. England J. Med. 319:1676–1680).

The present invention relates to compositions and methods of adoptive immunotherapy for the prevention and/or treatment of primary and metastatic colon cancer in humans using macrophages sensitized to the antigenic CSG molecule of this invention, with or without non-covalent complexes of heat shock protein (hsp). Antigenicity or immunogenicity of the CSG of the invention is readily confirmed by the ability of the CSG protein or a fragment thereof to raise antibodies or educate naive effector cells, which in turn lyse target cells expressing the antigen (or epitope).

Cancer cells are, by definition, abnormal and contain proteins which should be recognized by the immune system as foreign since they are not present in normal tissues. However, the immune system often seems to ignore this abnormality and fails to attack tumors. The foreign CSG protein of this invention that are produced by the cancer cells can be used to reveal their presence. The CSG is broken into short fragments, called tumor antigens, which are displayed on the surface of the cell. These tumor antigens are held or presented on the cell surface by molecules called MHC, of which there are two types: class I and II. Tumor antigens in association with MHC class I molecules are recognized by cytotoxic T cells while antigen-MHC class II complexes are recognized by a second subset of T cells called helper cells. These cells secrete cytokines which slow or stop tumor growth and help another type of white blood cell, B cells, to make antibodies against the tumor cells.

In adoptive immunotherapy, T cells or other antigen presenting cells (APCs) are stimulated outside the body (ex vivo), using the tumor specific CSG antigens of the present invention. The stimulated cells are then reinfused into the patient where they attack the cancerous cells. Research has shown that using both cytotoxic and helper T cells is far more effective than using either subset alone. Additionally, the CSG antigen may be complexed with heat shock proteins to stimulate the APCs as described in U.S. Pat. No. 5,985,270.

The APCs can be selected from among those antigen presenting cells known in the art, including but not limited to macrophages, dendritic cells, B lymphocytes, and a combination thereof, and are preferably macrophages. In a preferred use, wherein cells are autologous to the individual, autologous immune cells such as lymphocytes, macrophages or other APCs are used to circumvent the issue of whom to select as the donor of the immune cells for adoptive transfer. Another problem circumvented by use of autologous immune cells is graft versus host disease which can be fatal if unsuccessfully treated.

In adoptive immunotherapy with gene therapy, DNA of the CSG of the invention can be introduced into effector cells similarly as in conventional gene therapy. This can enhance the cytotoxicity of the effector cells to tumor cells as they have been manipulated to produce the antigenic protein resulting in improvement of the adoptive immunotherapy.

CSG antigens of this invention are also useful as components of colon cancer vaccines. The vaccine comprises an immunogenically stimulatory amount of a CSG antigen of the present invention. Immunogenically stimulatory amount refers to that amount of antigen that is able to invoke the desired immune response in the recipient for the amelioration, or treatment of colon cancer. Effective amounts may be determined empirically by standard procedures well known to those skilled in the art.

The CSG antigen can be provided in any one of a number of vaccine formulations which are designed to induce the desired type of immune response, e.g., antibody and/or cell mediated. Such formulations are known in the art and include, but are not limited to, formulations such as those described in U.S. Pat. No. 5,585,103. Vaccine formulations of the present invention used to stimulate immune responses can also include pharmaceutically acceptable adjuvants.

What is claimed is:

1. A method for detecting the presence of colon cancer in a patient comprising
   (a) determining levels of a polynucleotide comprising SEQ ID NO:1 or a polypeptide encoded thereby, in cells, tissues or bodily fluids in a patient; and
   (b) comparing the determined levels of the polynucleotide comprising SEQ ID NO:1 or the polypeptide encoded thereby with levels of the polypeptide comprising SEQ ID NO:1 or the polypeptide encoded thereby in cells, tissues or bodily fluids measured in a normal human control, wherein a change in determined levels of the polynucleotide comprising SEQ ID NO:1 or the polypeptide encoded thereby in said patient versus levels of the polynucleotide comprising SEQ ID NO:1 or the polypeptide encoded thereby measured in a normal human control is associated with the presence of colon cancer.

* * * * *

SEQUENCE LISTING

<160> NUMBER OF SEQ ID NOS: 1

<210> SEQ ID NO 1
<211> LENGTH: 2608
<212> TYPE: DNA
<213> ORGANISM: Homo sapiens
<220> FEATURE:
<221> NAME/KEY: unsure
<222> LOCATION: (2025)
<221> NAME/KEY: unsure
<222> LOCATION: (2036)
<221> NAME/KEY: unsure
<222> LOCATION: (2163)
<221> NAME/KEY: unsure
<222> LOCATION: (2263)

<400> SEQUENCE: 1

| | | | | | | |
|---|---|---|---|---|---|---|
| gctgatagca | cagttctgtc | cagagaagga | aggcggaata | aacttattca | ttcccaggaa | 60 |
| ctcttggggt | aggtgtgtgt | ttttcacatc | ttaaaggctc | acagaccctg | cgctggacaa | 120 |
| atgttccatt | cctgaaggac | ctctccagaa | tccggattgc | tgaatcttcc | ctgttgccta | 180 |
| gaagggctcc | aaaccacctc | ttgacaatgg | gaaactgggt | ggttaaccac | tggttttcag | 240 |
| ttttgtttct | ggttgtttgg | ttagggctga | atgttttcct | gtttgtggat | gccttcctga | 300 |
| aatatgagaa | ggccgacaaa | tactactaca | caagaaaaat | ccttgggtca | acattggcct | 360 |
| gtgcccgagc | gtctgctctc | tgcttgaatt | ttaacagcac | gctgatcctg | cttcctgtgt | 420 |
| gtcgcaatct | gctgtccttc | ctgaggggca | cctgctcatt | ttgcagccgc | acactgagaa | 480 |
| agcaattgga | tcacaacctc | accttccaca | agctggtggc | ctatatgatc | tgcctacata | 540 |
| cagctattca | catcattgca | cacctgttta | actttgactg | ctatagcaga | agccgacagg | 600 |
| ccacagatgg | ctcccttgcc | tccattctct | ccagcctatc | tcatgatgag | aaaaaggggg | 660 |
| gttcttggct | aaatcccatc | cagtcccgaa | acacgacagt | ggagtatgtg | acattcacca | 720 |
| gcgttgctgg | tctcactgga | gtgatcatga | caatagcctt | gattctcatg | gtaacttcag | 780 |
| ctactgagtt | catccggagg | agttattttg | aagtcttctg | gtatactcac | cacctttta | 840 |
| tcttctatat | ccttggctta | gggattcacg | gcattggtgg | aattgtccgg | ggtcaaacag | 900 |
| aggagagcat | gaatgagagt | catcctcgca | agtgtgcaga | gtcttttgag | atgtgggatg | 960 |
| atcgtgactc | ccactgtagg | cgccctaagt | ttgaagggca | tcccctgag | tcttggaagt | 1020 |
| ggatccttgc | accggtcatt | ctttatatct | gtgaaaggat | cctccggttt | taccgctccc | 1080 |
| agcagaaggt | tgtgattacc | aaggttgtta | tgcacccatc | caaagttttg | gaattgcaga | 1140 |
| tgaacaagcg | tggcttcagc | atggaagtgg | ggcagtatat | ctttgttaat | tgcccctcaa | 1200 |
| tctctctcct | ggaatggcat | ccttttactt | tgacctctgc | tccagaggaa | gatttcttct | 1260 |
| ccattcatat | ccgagcagca | ggggactgga | cagaaaatct | cataagggct | ttcgaacaac | 1320 |
| aatattcacc | aattcccagg | attgaagtgg | atggtcccct | tggcacagcc | agtgaggatg | 1380 |
| ttttccagta | tgaagtggct | gtgctggttg | gagcaggaat | tgggggtcacc | cccttttgctt | 1440 |
| ctatcttgaa | atccatctgg | tacaaattcc | agtgtgcaga | ccacaacctc | aaaacaaaaa | 1500 |
| agatctattt | ctactggatc | tgcagggaga | caggtgcctt | ttcctggttc | aacaacctgt | 1560 |
| tgacttccct | ggaacaggag | atggaggaat | taggcaaagt | gggttttcta | aactaccgtc | 1620 |
| tcttcctcac | cggatgggac | agcaatattg | ttggtcatgc | agcattaaac | tttgacaagg | 1680 |
| ccactgacat | cgtgacaggt | ctgaaacaga | aaacctcctg | tggagaccca | atgtgggaca | 1740 |

```
atgagttttc tacaatagct acctcccacc ccaagtctgt agtgggagtt ttcttatgtg    1800
gccctcggac tttggcaaag agcctgcgca aatgctgtca ccgatattcc agtctggatc    1860
ctagaaaggt tcaattctac ttcaacaaag aaaatttttg agttatagga ataaggacgg    1920
taatctgcat tttgtctctt tgtatcttca gtaattgagt tataggaata aggacggtaa    1980 tctgcattt gtctctttgt atcttcagta atttacttgg tctcntcagg tttgancagt    2040
cactttagat aagaatgtgc ctctcaagcc ttgactccct ggtattcttt ttttgattgc    2100
attcaacttc gttacttgag cttcagcaac ttaagaactt ctgaagttct taaagttctg    2160
aanttcttaa agcccatgga tcctttctca gaaaaataac tgtaaatctt tctggacagc    2220
catgactgta gcaaggcttg atagcagaag tttggtggtt canaattata caactaatcc    2280
caggtgattt tatcaattcc agtgttacca tctcctgagt tttggtttgt aatcttttgt    2340
ccctcccacc cccacagaag attttaagta gggtgacttt ttaaataaaa atttattgaa    2400
taattaatga taaaacataa taataaacat aaataataaa caaaattacc gagaacccca    2460
tccccatata acaccaacag tgtacatgtt tactgtcact tttgatatgg tttatccagt    2520
gtgaacagca atttattatt tttgctcatc aaaaaataaa ggattttttt tcacttgaaa    2580
aaaaaaaaaa aaaaaaaaaa aaaaaaaa                                       2608
```